US009753193B2

(12) United States Patent
Tabirian et al.

(10) Patent No.: US 9,753,193 B2
(45) Date of Patent: Sep. 5, 2017

(54) METHODS AND APPARATUS FOR HUMAN VISION CORRECTION USING DIFFRACTIVE WAVEPLATE LENSES

(71) Applicant: Beam Engineering for Advanced Measurements Co., Winter Park, FL (US)

(72) Inventors: Nelson V. Tabirian, Winter Park, FL (US); Anna Tabirian, Winter Park, FL (US); David E. Roberts, Apopka, FL (US)

(73) Assignee: Beam Engineering for Advanced Measurements Co., Orland, FL (US)

( * ) Notice: Subject to any disclaimer, the term of this patent is extended or adjusted under 35 U.S.C. 154(b) by 0 days.

(21) Appl. No.: 14/688,540

(22) Filed: Apr. 16, 2015

(65) Prior Publication Data
US 2015/0301356 A1 Oct. 22, 2015

Related U.S. Application Data

(60) Provisional application No. 61/980,062, filed on Apr. 16, 2014.

(51) Int. Cl.
| | | |
|---|---|---|
| *A61F 2/16* | (2006.01) | |
| *G02C 7/02* | (2006.01) | |
| *G02B 5/18* | (2006.01) | |
| *G02C 7/06* | (2006.01) | |
| *G02C 7/12* | (2006.01) | |
| *G02C 7/08* | (2006.01) | |
| *G02B 5/30* | (2006.01) | |

(Continued)

(52) U.S. Cl.
CPC .......... *G02B 5/1833* (2013.01); *A61F 2/1654* (2013.01); *G02B 3/0081* (2013.01);
(Continued)

(58) Field of Classification Search
CPC .......... G02C 1/022; G02C 7/041; G02C 7/06; G02C 7/068; A61F 2/1654;
(Continued)

(56) References Cited

U.S. PATENT DOCUMENTS

| 2,435,616 A | 2/1948 | Vittum |
| 3,721,486 A | 3/1973 | Bramley |

(Continued)

FOREIGN PATENT DOCUMENTS

| EP | 1970734 | 9/2008 |
| EP | 2088456 | 12/2009 |

(Continued)

OTHER PUBLICATIONS

Tabirian, et al., PCT Application No. PCT/US15/26186 filed Apr. 16, 2015, Notification of Transmittal of the International Search Report and the Written Opinion of the International Searching Authority mailed Jul. 14, 2015, 17 pages.

(Continued)

*Primary Examiner* — Paul Prebilic
(74) *Attorney, Agent, or Firm* — Brian S. Steinberger; Law Offices of Brian S. Steinberger, P.A.

(57) ABSTRACT

Lenses, devices, apparatus, systems, methods of manufacturing and fabricating an ophthalmic lens device for correction of human vision. The ophthalmic lens device includes at least one diffractive waveplate coating with an optical axis orientation pattern designed to correct the vision of individual patients. The ophthalmic lens device including diffractive waveplate coating may also provide a portion of the required vision correction by means of refraction of light by curved surfaces of a dielectric material.

18 Claims, 10 Drawing Sheets

(51) Int. Cl.
| | |
|---|---|
| *G02B 27/42* | (2006.01) |
| *G02B 5/00* | (2006.01) |
| *G02B 6/024* | (2006.01) |
| *G02B 6/35* | (2006.01) |
| *G02B 3/00* | (2006.01) |
| *G02B 3/10* | (2006.01) |
| *G02C 7/10* | (2006.01) |

(52) U.S. Cl.
CPC ............... *G02B 3/10* (2013.01); *G02B 5/001* (2013.01); *G02B 5/1828* (2013.01); *G02B 5/3083* (2013.01); *G02B 6/024* (2013.01); *G02B 6/3534* (2013.01); *G02B 6/3592* (2013.01); *G02B 27/4205* (2013.01); *G02B 27/4211* (2013.01); *G02B 27/4216* (2013.01); *G02B 27/4261* (2013.01); *G02C 7/022* (2013.01); *G02C 7/061* (2013.01); *G02C 7/086* (2013.01); *G02C 7/12* (2013.01); *G02C 7/10* (2013.01); *G02C 2202/16* (2013.01); *G02C 2202/20* (2013.01)

(58) Field of Classification Search
CPC .. G02B 27/4216; G02B 5/1828; G02B 6/024; G02B 6/3534; G02B 2207/117; G02B 2207/123; G02B 2207/125; G02B 2207/129; G02B 5/1833; G02B 5/3083; G02B 27/4211

See application file for complete search history.

(56) References Cited

U.S. PATENT DOCUMENTS

| | | | |
|---|---|---|---|
| 3,897,136 | A | 7/1975 | Bryngdahl |
| 4,160,598 | A | 7/1979 | Firester et al. |
| 4,301,023 | A | 11/1981 | Schuberth |
| 4,956,141 | A | 9/1990 | Allen |
| 4,983,332 | A | 1/1991 | Hahn |
| 5,032,009 | A | 7/1991 | Gibbons |
| 5,042,950 | A | 8/1991 | Salmon, Jr. |
| 5,047,847 | A | 9/1991 | Toda |
| 5,100,231 | A | 3/1992 | Sasnett et al. |
| 5,142,411 | A * | 8/1992 | Fiala .................. A61F 2/1618 351/159.05 |
| 5,218,610 | A | 6/1993 | Dixon |
| 5,325,218 | A | 6/1994 | Willett |
| 5,446,596 | A | 8/1995 | Mostrorocco |
| 5,621,525 | A | 4/1997 | Vogeler et al. |
| 5,895,422 | A * | 4/1999 | Hauber ................ A61F 2/1613 351/159.11 |
| 5,903,330 | A | 5/1999 | Funfschilling |
| 5,989,758 | A | 11/1999 | Komatsu |
| 6,107,617 | A | 8/2000 | Love et al. |
| 6,139,147 | A * | 10/2000 | Zhang ..................... G02B 5/32 264/1.31 |
| 6,320,663 | B1 | 11/2001 | Ershov |
| 6,452,145 | B1 | 9/2002 | Graves et al. |
| 6,551,531 | B1 | 4/2003 | Ford |
| 6,678,042 | B2 | 1/2004 | Tabirian et al. |
| 6,728,049 | B1 | 4/2004 | Tabirian et al. |
| 6,792,028 | B2 | 9/2004 | Cook |
| 7,048,619 | B2 | 5/2006 | Park |
| 7,094,304 | B2 | 8/2006 | Nystrom |
| 7,196,758 | B2 | 3/2007 | Crawford |
| 7,319,566 | B2 | 1/2008 | Prince |
| 7,324,286 | B1 | 1/2008 | Glebov |
| 7,764,426 | B2 | 7/2010 | Lipson |
| 8,045,130 | B2 | 10/2011 | Son |
| 8,077,388 | B2 | 12/2011 | Gerton |
| 8,264,623 | B2 | 9/2012 | Marrucci |
| 8,520,170 | B2 | 8/2013 | Escuti |
| 8,643,822 | B2 | 2/2014 | Tan et al. |
| 8,982,313 | B2 | 3/2015 | Escuti et al. |
| 9,541,772 | B2 | 1/2017 | De Sio et al. |
| 9,557,456 | B2 | 1/2017 | Tabirian et al. |
| 9,592,116 | B2 | 3/2017 | De Sio et al. |
| 9,617,205 | B2 | 4/2017 | Tabirian et al. |
| 2001/0002895 | A1 | 6/2001 | Kawano |
| 2001/0018612 | A1* | 8/2001 | Carson ................. A61F 2/1654 623/5.11 |
| 2001/0030720 | A1 | 10/2001 | Ichihashi |
| 2002/0027624 | A1 | 3/2002 | Seiberle |
| 2002/0167639 | A1 | 11/2002 | Coates |
| 2003/0072896 | A1 | 4/2003 | Kwok |
| 2003/0152712 | A1 | 8/2003 | Motomura |
| 2003/0206288 | A1 | 11/2003 | Tabirian et al. |
| 2004/0105059 | A1 | 6/2004 | Ohyama |
| 2004/0165126 | A1 | 8/2004 | Ooi et al. |
| 2005/0110942 | A1 | 5/2005 | Ide |
| 2005/0219696 | A1 | 10/2005 | Albert et al. |
| 2005/0271325 | A1 | 12/2005 | Anderson et al. |
| 2006/0008649 | A1 | 1/2006 | Shinichiro |
| 2006/0055883 | A1 | 3/2006 | Morris |
| 2006/0222783 | A1 | 10/2006 | Hayashi |
| 2007/0032866 | A1 | 2/2007 | Portney |
| 2007/0115551 | A1 | 5/2007 | Spilman |
| 2007/0122573 | A1 | 5/2007 | Yasuike |
| 2007/0247586 | A1 | 10/2007 | Tabirian |
| 2007/0258677 | A1 | 11/2007 | Chigrinov |
| 2008/0226844 | A1 | 9/2008 | Shemo |
| 2008/0278675 | A1 | 11/2008 | Escuti |
| 2009/0073331 | A1 | 3/2009 | Shi |
| 2009/0122402 | A1 | 5/2009 | Shemo |
| 2009/0141216 | A1 | 6/2009 | Marrucci |
| 2009/0256977 | A1 | 10/2009 | Haddock |
| 2009/0257106 | A1 | 10/2009 | Tan |
| 2009/0264707 | A1 | 10/2009 | Hendriks |
| 2009/0268154 | A1 | 10/2009 | Meyers |
| 2010/0066929 | A1 | 3/2010 | Shemo |
| 2011/0075073 | A1 | 3/2011 | Oiwa |
| 2011/0097557 | A1 | 4/2011 | May |
| 2011/0109874 | A1 | 5/2011 | Piers |
| 2011/0135850 | A1 | 6/2011 | Saha |
| 2011/0234944 | A1 | 9/2011 | Powers |
| 2011/0262844 | A1 | 10/2011 | Tabirian |
| 2012/0075168 | A1* | 3/2012 | Osterhout ............ G02B 27/017 345/8 |
| 2012/0140167 | A1* | 6/2012 | Blum .................... A61F 2/1624 351/159.34 |
| 2012/0188467 | A1 | 7/2012 | Escuti |
| 2014/0055740 | A1 | 2/2014 | Spaulding |
| 2014/0211145 | A1* | 7/2014 | Tabirian ................. G02F 1/292 349/201 |
| 2014/0252666 | A1 | 9/2014 | Tabirian |
| 2015/0036084 | A1* | 2/2015 | Srivastava ........ G02F 1/133753 349/96 |
| 2015/0077700 | A1 | 3/2015 | De Sio |
| 2015/0081016 | A1 | 3/2015 | De Sio |
| 2015/0276997 | A1 | 10/2015 | Tabirian et al. |
| 2016/0011353 | A1* | 1/2016 | Escuti ................. G02B 27/283 359/15 |
| 2016/0023993 | A1 | 1/2016 | Tabirian |
| 2016/0209560 | A1* | 7/2016 | Tabirian ................ G02C 7/022 |
| 2016/0231592 | A9* | 8/2016 | Beaton .................. A61F 2/1627 |

FOREIGN PATENT DOCUMENTS

| | | |
|---|---|---|
| EP | 2848979 A2 | 3/2015 |
| EP | 2848979 A3 | 3/2015 |
| EP | 2851737 A1 | 3/2015 |
| GB | 2209751 | 5/1989 |
| JP | 2001142033 | 5/2001 |
| JP | 2004226752 | 8/2004 |
| WO | 2008130555 | 10/2008 |
| WO | 2008130559 | 10/2008 |

OTHER PUBLICATIONS

Heller, A., A Gian Leap for Space Telescopes, Lawrence Livermore National Laboratory, Foldable Optics, S&TR, Mar. 2003, pp. 12-18.

(56) References Cited

OTHER PUBLICATIONS

Tabiryan, N., et al., Thin Waveplate Lenses of Switchable Focal Length—New Generation in Optics, Optics Express, Sep. 2015, 12 pages, vol. 23, No. 20.
Tabiryan, N., et al., Broadband Waveplate Lenses, Optics Express, Mar. 2016, 12 pages, vol. 24, No. 7.
Tabiryan, N., et al., Superlens in the skies: liquid-crystal-polymer technology for telescopes, SPIE, 2016, 2 pages. (Feb. 2016).
Honma, M., et al., Liquid-Crystal Fresnel Zone Plate Fabricated by Microrubbing, Japanese Journal of Applied Physics, 2005, pp. 287-290, vol. 44, No. 1A, 4 pages.
Nersisyan, S.R., et al., The Principles of Laser Beam Control with Polarization Gratings Introduced as Diffractive Waveplates, Proc. of SPIE, vol. 7775, 10 pages.
Marrucci, L., et al., Pancharatnam-Berry Phase Optical Elements for Wavefront Shaping in the Visible Domain: Switchable Helical Modes Generation, Physics.Optics, Dec. 2007, 9 pages.
Beam Engineering for Advanced Measurements Co., European Patent Application No. 15779550.1-1562, filed Nov. 15, 2016, Supplementary Extended Search Report dated Mar. 8, 2017, 13 pages.
Tabiryan, et al., The Promise of Diffractive Waveplates, OPN Optics and Photonics News, Mar. 2010, 6 pages.
Nersisyan, et al., Study of azo dye surface command photoalignment material for photonics applications, Applied Optics, vol. 49, No. 10, Apr. 1, 2010, 8 pages.
Nersisyan, et al., Characterization of optically imprinted polarization gratings, Applied Optics, vol. 48, No. 21, Jul. 20, 2009, 6 pages.
Nersisyan, et al., Fabrication of Liquid Crystal Polymer Axial Waveplates for UV-IR Wavelengths, Optics Express, vol. 17, No. 14, Jul. 2009, 9 pages.
Nersisyan, et al., Polarization insensitive imaging through polarization gratings, Optics Express, vol. 17, No. 3, Feb. 2, 2009, 14 pages.
Sarkissian, et al., Longitudinally modulated nematic bandgap structure, Optical Society of America, vol. 23, No. 8, Aug. 2008, 6 pages.
Sarkissian, et al., Polarization-universal bandgap in periodically twisted nematics, Optics Letters, vol. 31, No. 11, Jun. 1, 2006, abstract, 4 pages.
Sarkissian, et al., Polarization-Controlled Switching Between Diffraction Orders in Transverse-Periodically Aligned Nematic Liquid Crystals, Optics Letters, Aug. 2006, abstract, 4 pages.
Schadt, et al., Photo-Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.
Schadt, et al., Photo-Generation of Linearly Polymerized Liquid Crystal Aligning Layers Comprising Novel, Integrated Optically Patterned Retarders and Color Filters, Jpn. J. Appl. Phys., vol. 34, Part 1, No. 6A, Jun. 1995, 10 pages.
Schadt, et al., Optical patterning of multi-domain liquid-crystal displays with wide viewing angles, Nature, vol. 381, May 16, 1996, 4 pages.
Escuti, et al., Polarization-Independent LC Microdisplays Using Liquid Crystal Polarization Gratings: A Viable Solution (?), Dept of Electrical & Computer Engineering @ ILCC, Jul. 1, 2008, 30 pages.
Gibbons, et al., Surface-mediated alignment of nematic liquid crystals with polarized laser light, Nature, vol. 351, May 2, 1991, 1 page.
Gibbons, et al., Optically generated liquid crystal gratings, Appl. Phys. Lett., 65, Nov. 14, 1994, 3 pages.
University of Central Florida, School of Optics CREOL PPCE, Optics in the Southeast, Technical Conference and Tabletop Exhibit, Nov. 12-13, 2003, 9 pages.
Zel'dovich, et al., Devices for displaying visual information, Disclosure, School of Optics/CREOL, University of central Florida, Jul. 2000, 10 pages.
Titus, et al, Efficient polarization-independent, re ective liquid crystal phase grating, Applied Physics Letter 71, Oct. 20, 1997, 3 pages.
Chen, et al. An Electrooptically Controlled Liquid-Crystal Diffraction Grating, Applied Physics Letter 67, Oct. 30, 1995, 4 pages.

Kim, et al., Unusual Characteristics of Diffraction Gratings in a Liquid Crystal Cell, Advanced Materials, vol. 14, No. 13-14, Jul. 4, 2002, 7 pages.
Pan, et al., Surface Topography and Alignment Effects in UV-Modified Polyimide Films with Micron Size Patterns, Chinese Journal of Physics, vol. 41, No. 2, Apr. 2003, 8 pages.
Fuh, et al., Dynamic studies of holographic gratings in dye-doped liquid-crystal films, Optics Letter, vol. 26, No. 22, Nov. 15, 2001, 3 pages.
Wen, et al., Nematic liquid-crystal polarization gratings by modification of surface alignment, Applied Optics, vol. 41, No. 7, Mar. 1, 2002, 5 pages.
Anagnostis, et al., Replication produces holographic optics in volume, Laser Focus World, vol. 36, Issue 3, Mar. 1, 2000, 6 pages.
Gale, Replicated Diffractive Optics and Micro-Optics, Optics and Photonics News, Aug. 2003, 6 pages.
McEldowney, et al., Creating vortex retarders using photoaligned LC polymers, Optics Letter, vol. 33, No. 2, Jan. 15, 2008, 3 pages.
Kakichashvili, et al., Method for phase polarization recording of holograms, Sov. J. Quantum. Electron, vol. 4, No. 6, Dec. 1974, 5 pages.
Todorov, et al., High-Sensitivity Material With Reversible Photo-Induced Anisotropy, Optics Communications, vol. 47, No. 2, Aug. 15, 1983, 4 pages.
Attia, et al., Anisoptropic Gratings Recorded From Two Circularly Polarized Coherent Waves, Optics Communications, vol. 47, No. 2, Aug. 15, 1983, 6 pages.
Cipparrone, et al., Permanent polarization gratings in photosensitive langmuir blodget films, Applied Physics Letter, vol. 77, No. 14, Oct. 2, 2000, 4 pages.
Lee et al., "Generation of pretilt angles of liquid crystals on cinnamte-based photoalignment . . . ", Opt., Expr., vol. 17 (26) (Dec. 2009), abstract, 4 pages.
Chigrinov et al., "Anchoring properties of photoaligned azo-dye materials" Phys. Rev., E vol. 68, (Dec. 2003), 5 pages.
Pagliusi et al. Surface-induced photorefractivity in twistable nematics: toward the all-optical control of gain, Opt. Expr. vol. 16, Oct. 2008, 9 pages.
Anderson, G., et al., Broadband Antihole Photon Sieve Telescope, Applied Optics, vol. 16, No. 18., Jun. 2007, 3 pages.
Early, J. et al., Twenty Meter Space Telescope Based on Diffractive Fresnel Lens, SPIE, U.S. Department of Energy, Lawrence Livermore National Laboratory, Jun. 2003, 13 pages.
Martinez-Cuenca, et al., Reconfigurable Shack-Hartmann Sensor Without Moving Elements,Optical Society of America, vol. 35, No. 9, May 2010, 3 pages.
Serak, S., et al., High-efficiency 1.5 mm Thick Optical Axis Grating and its Use for Laser Beam Combining, Optical Society of America, vol. 32, No., Jan. 2007, 4 pages.
Ono et al., Effects of phase shift between two photoalignment substances on diffration properties in liquid crystalline grating cells, Appl. Opt. vol. 48, Jan. 2009, 7 pgs.
Nersisyan, S., et al., Polarization insensitive imaging through polarization gratins, Optics Express, vol. 17, No. 3, Feb. 2 ,2009, 14 pages.
Oise, Optics in the Southeast, Technical Conference and Tabletop Exhibit, Optical Society of America, Orlando, FL., Nov. 12-13, 2003, 9 pages.
Tabiryan, et al., Fabricating Vector Vortex Waveplates for Coronagraphy, Jan. 2012, 12 pages.
Nersisyan, et al., Optical Axis Gratings in Liquid Crystals and Their Use for Polarization Insensitive Optical Switching, Journal of Nonlinear Optical Physics & Materials, vol. 18, No. 1, Jul. 2009, 47 pages.
Sarkissian, et al., Periodically Aligned Liquid Crystal: Potential Application for Projection Displays, Mol. Cryst. Liq. Cryst., vol. 451, Aug. 2006, 19 pages.
Sarkissian, et al., Potential application of Periodically Aligned Liquid Crystal cell for projection displays, JThE12, May 2005, 3 pages.
Escuti, et al., A Polarization-Independent Liquid Crystal Saptial-Light-Modulator, Liquid Crystals X, Proc. of SPIE, vol. 6332, Sep. 15, 2006, 9 pages.

(56) References Cited

OTHER PUBLICATIONS

Escuti, et al., Simplified Spectropolarimetry Using Reactive Mesogen Polarization Gratings, Imaging Spectrometry XI, Proc. of SPIE, vol. 6302, Sep. 1, 2006, 11 pages.

Gibbons, et al., Optically Controlled Alignment of Liquid Crystals: Devices and Applications, Molecular Crystals and Liquid Crystals, vol. 251, Sep. 1994, 19 pages.

Ichimura, et al., Surface assisted photoalignment control of lyotropic liquid crystals, Part 1, Characterization and photoalignment of aqueous solutions of a water soluble dyes as lyotropic liquid crystals, J. Materials. Chem., vol. 12, Dec. 2002, abstract, 2 pages.

Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, Feb. 1988, 3 pages.

Provenzano, et al., Highly efficient liquid crystal based diffraction grating induced by polarization holograms at the aligning surfaces, Applied Physics Letter 89, Sep. 2006, 4 pages.

Yu, et al., Polarization Grating of Photoaligned Liquid Crystals with Oppositely Twisted Domain Structures, Molecular Crystals Liquid Crystals, vol. 433, Jun. 28, 2005, 7 pages.

Crawford, et al., Liquid-crystal diffraction gratings using polarization holography alignment techniques, Journal of Applied Physics 98, Dec. 2005, 10 pages.

Seiberle, et al., 38.1 Invited Paper: Photo-Aligned Anisotropic Optical Thin Films, SID 03 Digest, Mar. 2004, 4 pages.

Stalder, et al., Lineraly polarized light with axial symmetry generated by liquid-crystal polarization converters, Optics Letters vol. 21, No., Jul. 1996, 3 pages.

Nikolova, et al., Diffraction Efficiency and Selectivity of Polarization Holographic Recording, Optica Acta: International Journal of Optics, vol. 31, No. 5, May 1984, 11 pages.

Yaroshchuk et al. "Azodyes as photoalignment agents for polymerizable liquid crystals", IDW'06 Digest vol. 1-3, May 2006, 3 pages.

M. Honma, T. Nose, Polarization-independent liquid crystal grating fabricated by microrubbing process, Jpn. J. Appl. Phys., Part 1, vol. 42, Nov. 2003, 3 pages.

Naydenova et al., Diffraction form polarization holographic gratings with surface relief in side chain azobenzene polyesters, J. Pot. Soc. Am. B, vol. 15, Apr. 1, 1998, 14 pages.

Oh et al., Achromatic polarization gratings as highly efficent thin-film polarizing beamsplitters for broadband light Proc. SPIE vol. 6682, Sep. 13, 2007, 4 pages.

Dierking, Polymer Network-Stabilized Liquid Crystals, Advanced Materials, vol. 12, No. 3, Jan. 24, 2000, 15 pages.

Blinov, et al., Electrooptic Effects in Liquid Crystal Materials, Springer-Verlag New York, Jan. 1, 1994, 17 pages.

Crawford, et al., Liquid Crystals in Complex Geometries; Formed by Polymer and Porous Networks, Taylor and Francis, Apr. 29, 1996, 4 pages.

Honma, et al., Liquid-Crystal Fresnel Zone Plate Fabricated by Microorubbing, Japanese Journal of Applied Phsyics, vol. 44, No. 1A, Jan. 2005, 4 pages.

\* cited by examiner

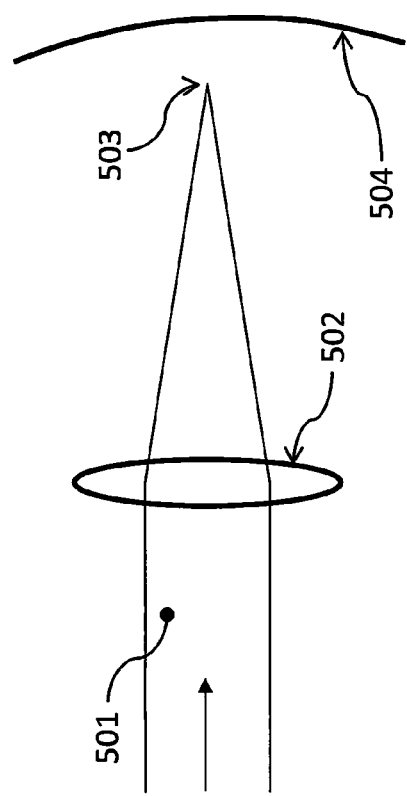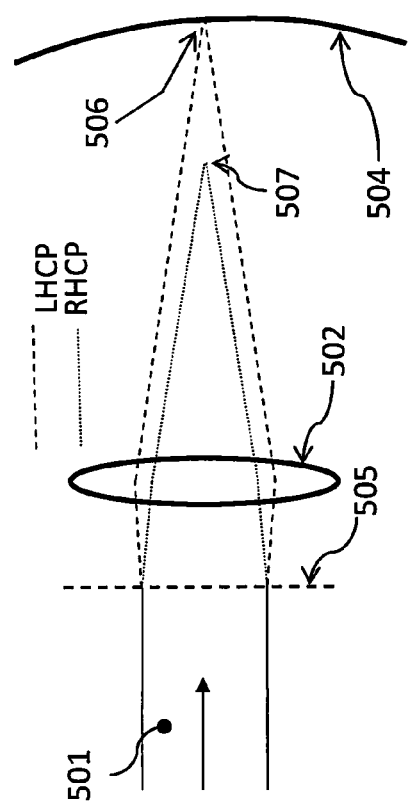
FIG. 5A
FIG. 5B

METHODS AND APPARATUS FOR HUMAN VISION CORRECTION USING DIFFRACTIVE WAVEPLATE LENSES

CROSS REFERENCE TO RELATED APPLICATIONS

This application claims the benefit of priority to U.S. Provisional Application Ser. No. 61/980,062 filed Apr. 16, 2014, the entire application of which is incorporated by reference in its' entirety.

GOVERNMENT LICENSE RIGHTS

This invention was made with government support under Army Contract No. W911QY-12-C-0016. The government has certain rights in this invention.

FIELD OF THE INVENTION

This invention relates to optical lenses, and in particular to systems, devices, apparatus, and methods for manufacturing and fabricating an ophthalmic lens device incorporating thin-film diffractive waveplate elements and, more specifically, in some examples, the fabrication of spectacles and other vision correction devices using optical photoalignment and polymerization of a thin layer of polymerizable liquid crystal in a laminated structure.

BACKGROUND OF THE INVENTION

Traditionally, ophthalmic lenses such as spectacles for correction of human vision have required curved optical surfaces of dielectric materials such as glass or plastic. The same is true for devices that combine vision correction with other functions; such devices include prescription sunglasses, prescription swimming goggles, prescription skiing googles, and goggles that combine both protection from ballistic projectiles and vision correction. All such ophthalmic devices depend on the refraction of light by dielectric media. Typically, fabrication of the lenses of such devices is time-consuming and expensive since it requires grinding, polishing, and/or molding of the glass or plastic optics in order to create curved surfaces that refract the light as needed. Thus, there is a need for lenses that could be obtained in the form of thin film structurally continuous coatings on a variety of substrates, and for methods of creating ophthalmic lens functionality quickly and at low cost.

Related art for intraocular lenses, that is, lenses that are surgically implanted into a patient's eye to replace a defective or missing natural eye lens, includes intraocular lenses that employ diffractive coatings that provide multiple focal regions, providing simultaneous high-quality vision for both near and far objects. The present invention provides an alternative method for providing multiple focal ranges, with methods that are inherently less difficult to fabricate and lower cost.

Thus, the need exists for solutions to the above problems with the prior art.

SUMMARY OF THE INVENTION

A primary objective of the present invention is to provide systems, devices, and methods for correction of human vision using thin-film diffractive waveplate coatings.

A secondary objective of the present invention is to provide systems, devices, and methods for an ophthalmic lens device which includes a thin-film coating, either on the surface of a locally flat optical substrate such as glass or plastic, or as a thin layer laminated between two locally flat optical substrates such as glass or plastic. The present invention also includes disclosure of methods for manufacturing said ophthalmic lens device. Said ophthalmic lens device may be either configured as spectacles external to the eye, or implanted surgically as an intraocular lens.

The present invention depends on the fact that light traversing a thin layer of transparent, anisotropic material will be deflected if the layer imposes approximately one-half wave of optical retardation on the light, and if the optical axis of the material in the anisotropic layer is spatially modulated in an appropriate manner. The optical axis orientation can be modulated in the required way by use of photoalignment materials such as the PAAD series of azobenzene-based compounds available from Beam Engineering for Advanced Measurements Co. (BEAM Co.) The local beam deflection angle θ is governed by the Bragg diffraction condition given by the following equation:

$$\theta = \pm \arcsin(\lambda/\Lambda) \quad (I)$$

Equation (I) is for the case in which the direction of propagation of the incoming light is perpendicular to the thin patterned optically anisotropic layer. In Equation (I), λ is the wavelength of the light and Λ is the local period of the continuously modulated optical axis orientation, i.e. the distance over which the orientation of the optical axis changes by 180° in a particular localized region of the pattern. The direction and magnitude of the deflection of light will depend on transverse location because in general, the orientation and period of the optical axis modulation pattern will depend on transverse location.

The sign of the beam deflection angle θ in Eq. (I) depends on the circular polarization state of the incident light. The light from both naturally illuminated scenes and artificially illuminated scenes is typically unpolarized, so part of the light reaching any specific point on the vision correction device will be deflected by the patterned surface in one direction, and part of the light will be deflected in the opposite direction, as indicated by the symbol ± in Equation (I). This effect must be considered in usage of these thin-film optically-active materials, for example by filtering out one of the polarization components before it is incident on the eye, or by deliberately using the difference in the deflection of light for the two circular polarizations to create acceptable visual acuity for both near and far objects, without the fabrication complexity and expense of prior art methods.

The method of forming the spatially-patterned anisotropic half-wave layer is an important aspect of various examples of the invention. In the case in which said layer is a surface coating on a single substrate, the layer may be formed by first depositing a photoalignment layer (for example, PAAD-22 from BEAM Co.) on the substrate, photoaligning the layer with the required spatial pattern of linearly polarized light, then depositing a half-wave thick layer of a polymerizable liquid crystal. The molecules of the polymerizable liquid crystal will align with the molecules of the photoalignment layer, after which the polymerizable liquid crystal can be photopolymerized with ultraviolet (UV) radiation.

In addition to the possibility of forming the active spatially-patterned anisotropic half-wave layer as a surface coating, it is also possible to form the layer between two substrates. The method of fabrication in the case in which the anisotropic layer is between two substrates is similar to the method described above for the case in which the layer is a surface coating, except that when the thin film is formed between two substrates, both of the substrate surfaces adjacent to the patterned anisotropic layer may be coated with photoalignment material (for example, PAAD-22 from BEAM Co.).

Prior art methods for correcting the wide variety of human vision defects relied on grinding, polishing, and/or molding the surfaces of substrates such as glass or plastic in order to cause the light to refract in such a way that compensation for said vision defects is provided. With the present invention, the required vision correction is obtained by means of variations in the optical axis orientation pattern. Therefore, the requirements to grind, polish, or mold the substrate are completely eliminated by the present invention. This eliminates the time and expense associated with these prior art methods for human vision correction.

Prior art methods are capable of providing spectacles with progressive lenses, with high visual acuity for far objects when the user looks near horizontally, and high visual acuity for near objects when the user looks down. With prior art methods, provision of such progressive-focus spectacles required complex and expensive grinding and polishing operations on glass or plastic in order to provide continuously varying focal distance, depending on the angle through which the user views objects through the spectacles. With the present invention, it is possible to provide the equivalent continuously variable focal correction by merely changing the pattern of optical axis orientation on the lenses, allowing more cost-effective provision of such vision correction devices.

In some examples, only one linear polarization of light from the scene being viewed by the user of the vision correction device would be passed by a polarizing layer. The linearly polarized light would then be converted to circularly polarized light, using a broadband quarter-wave phase retarder. All of the circularly polarized light would therefore be corrected in the same manner, thereby assuring that all the light reaching the user's eyes has been processed in such as way as to optimally correct the user's vision.

As indicated in Equation (I), the angle through which light is deflected by a diffractive waveplate coating depends on the wavelength of the light. For persons who only need slight correction of their vision, the resulting chromatic aberrations would not be significant. For persons who need large corrections of their vision in order to see clearly, a combination of conventional refractive correction and supplementary correction with a diffractive waveplate coating may be used to provide an optimal combination of convenience, cost, and quality of correction.

BRIEF DESCRIPTION OF THE DRAWINGS

FIG. 5A illustrates an example of correction of myopia (nearsightedness) in a human eye using a thin film of anisotropic material with a pattern of optical axis orientation designed to focus or defocus light incident on the eye.

FIG. 5B illustrates an example of correction of myopia (nearsightedness) in a human eye using a thin film of anisotropic material with a pattern of optical axis orientation designed to focus or defocus light incident on the eye.

DETAILED DESCRIPTION OF THE INVENTION

Figure 1:
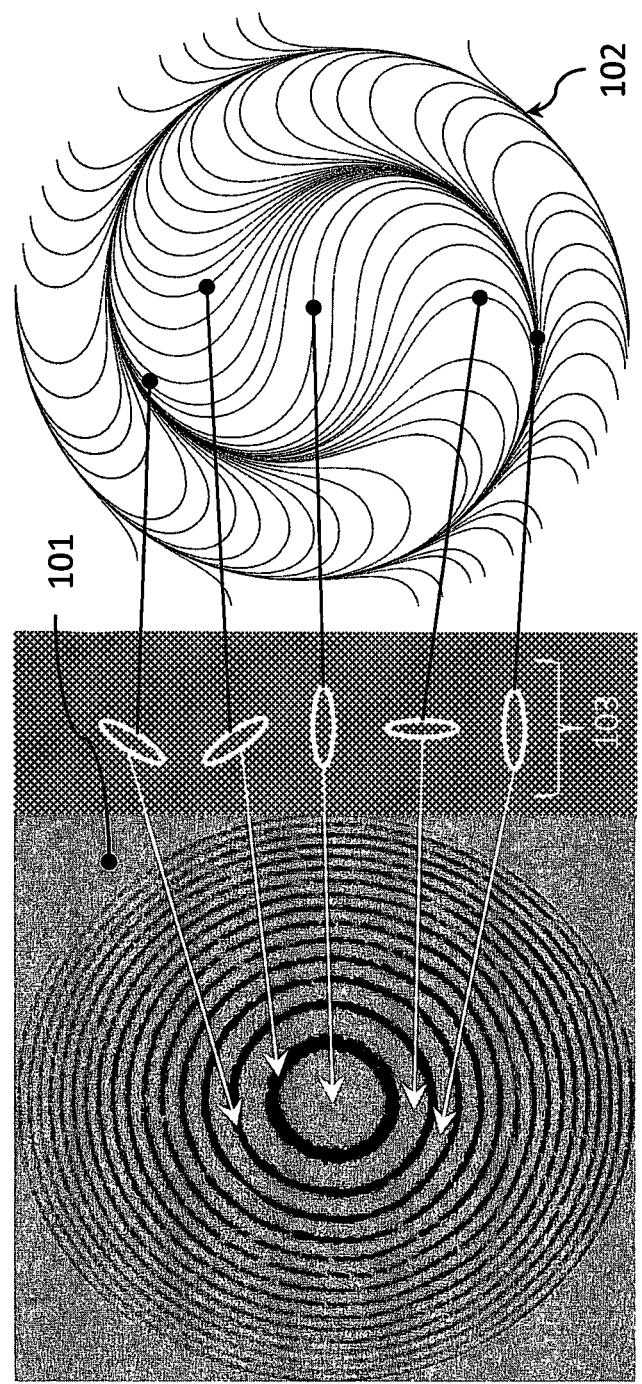
FIG. 1 illustrates the optical axis orientation of a diffractive waveplate lens.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

A list of components will now be described.
101 photograph
102 diagram
103 elliptical shapes
301 glasses/spectacles
302 lenses
303 pattern
401 light
402 lens
403 light
404 coating
405 multilayer structure
501 light
502 human eye lens
503 focus point
504 retina
505 diffractive waveplate coating
506 retina focus point
507 focus location
508 linear polarizer
509 homogeneous broadband quarter-wave plate
601 unpolarized light
602 conventional intraocular lens
603 a thin-film patterned diffractive waveplate coating
604 focus
605 retina
606 focus
611 focus
612 focus
621 homogeneous broadband quarter-wave plate
701 transparent portion
702 frame
703 optically-active layer
704 outer substrate
705 inner substrate
710 photoalignment layers
711 polymerizable liquid crystal
712 outer layer The present invention includes methods and apparatus for manufacturing an ophthalmic lens that forms a part of a device for correction of human vision. In addition, the present invention includes an ophthalmic lens, not located on the surface of the eye, in which optical correction is partially or entirely provided by a diffractive waveplate coating. Examples of such ophthalmic lenses are intraocular lenses, sunglasses, skiing goggles, swimming googles, and goggles designed for protection from ballistic projectiles.

The greatest potential benefit of patterned diffractive waveplates for correction of human vision is that vision correction is provided by a flat film of patterned anisotropic material only a few micrometers thick, instead of by a curved dielectric structure typically several millimeters thick as is the case with conventional vision correction devices. With techniques disclosed in the present invention, this thin, flat, patterned anisotropic layer can be created by purely optical means, completely eliminating the grinding, polishing, and/or molding processes that are necessary for the fabrication of such vision correction systems using prior art. In some embodiments of the present invention, vision correction is provided by a combination of both conventional refractive correction and correction by means of a diffractive waveplate coating.

According to the present invention, the methods for fabricating devices for vision correction are greatly simplified and thereby made much less expensive. Another benefit of the present invention is that if correction is provided solely by the diffractive waveplate coating, fabrication of the human vision correction device does not require equipment for grinding, polishing, or molding refractive elements. In other embodiments, in which human vision correction is provided by a combination of refractive elements and a diffractive waveplate coating, the number of standard refractive elements that must be stocked in order to service a large fraction of all customers could be greatly reduced.

This elimination of some of the equipment, processes, and inventory required for provision of devices for vision correction may allow the final configuration of a wide variety of eyewear at the point of sale, even from a vending machine, instead of requiring the customer to wait for the vision correction device to be fabricated at a remote laboratory or other facility.

One of the characteristics of light deflection by diffractive waveplate patterns is that the sign of the deflection angle is opposite for the two possible circular polarization states of light. This sign difference is represented by the plus-or-minus symbol in the expression on the right side of Equation (I). As a result of this characteristic, the sign of the focal length of a diffractive waveplate lens will be different for the two possible circular polarization states. For example, if the focal length of a diffractive waveplate lens is f for light with right-hand circular polarization (RHCP), then the focal length of the same lens for light with left-hand circular polarization (LHCP) will be −f. In the context of human vision correction, in which focus correction is measured in units of diopters, a lens that provides +1 diopter of focus change for RHCP light would provide −1 diopter of focus change for LHCP light. This is in contrast to the functioning of a conventional refractive lens, which has essentially the same focal length for all possible polarization states of light.

There are many possible approaches to incorporating the polarization properties of diffractive waveplate lenses into devices for human vision correction in such as way as to make these characteristics advantageous or at least acceptable. Two of these approaches will be disclosed in the present invention.

In those applications in which the amount of light available is sufficient, light of one of the states of polarization can be filtered out before it reaches the eye. With this approach, all of the light that reaches the user's eye will have been processed in the same way, so that the user sees only a single image corrected for his/her image defects. An example of an optical device for vision correction for which this approach would be acceptable is sunglasses.

In some other applications, it may be acceptable to present to the user's eye two images, with different focus characteristics. For persons with eyes that have limited ability to accommodate for changes in distance between the eyes and objects being viewed, having two images with different focal distances may be an advantage because it would allow the person to have at least one of the images in focus over a wider range of distances than would be the case with only a single image.

Referring to FIG. 1, the structure of a diffractive waveplate lens is revealed in a photograph 101 of such a lens between crossed polarizers. A diagram 102 illustrates the pattern of optical axis orientation in such a lens by means of continuous lines that at each point are tangent to the optical axis orientation at the corresponding transverse location in the diffractive waveplate lens. The underlying physical structure in the polymer layer that constitutes the diffractive waveplate lens is one in which the orientation of optically active liquid crystal molecules varies with transverse position. The orientation of these liquid crystal molecules is represented in FIG. 1 by the elliptical shapes 103. As indicated in FIG. 1, the spatially varying molecular axis orientation and consequent optical axis orientation change by approximately 90° from one dark ring to the next dark ring in the photograph 101, or from one light ring to the next light ring in that photograph.

Figure 2B:
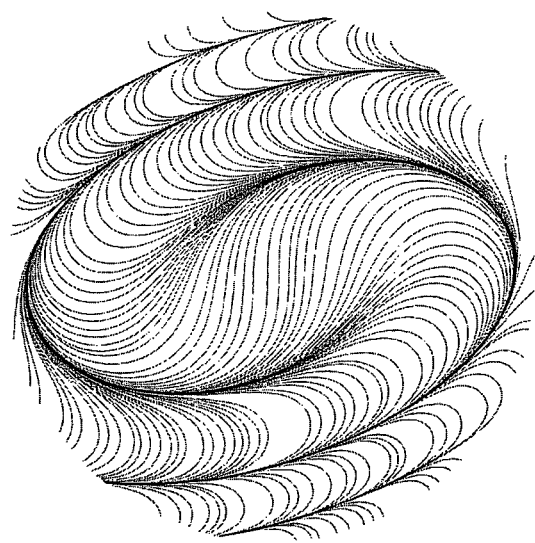
FIG. 2B illustrate exemplary optical axis orientation patterns in anisotropic optical films for correcting human vision.
Figure 2A:
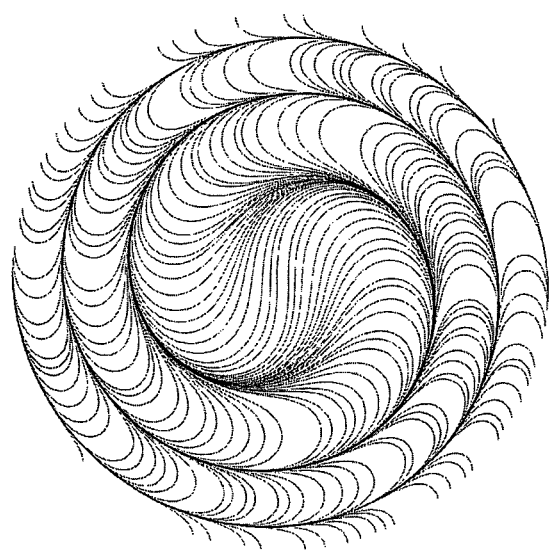
FIG. 2A illustrate exemplary optical axis orientation patterns in anisotropic optical films for correcting human vision.

Referring to FIGS. 2A and 2B, adjustment of the pattern of optical axis orientation in a diffractive waveplate lens allows the fabrication of a lens that combines the effect of a spherical refractive surface with aspheric modifications. In the example illustrated in FIG. 2A, the optical axis orientation pattern of a diffractive waveplate lens whose focusing characteristics are circularly symmetric is shown. The equivalent focusing characteristics could be achieved with prior art, using a lens with spherical refractive surfaces. In the example of FIG. 2B, the optical axis orientation pattern of a diffractive waveplate lens whose focusing characteristics are not circularly symmetric is shown. The equivalent focusing characteristics could only be achieved with prior art using a lens with aspherical refractive surfaces.

It is generally difficult and expensive to fabricate refractive optical components with aspherical surfaces. Focusing characteristics equivalent to those of the diffractive waveplate lens characterized by the pattern shown in FIG. 2B could only be achieved using prior art with a lens combining spherical and cylindrical curvature. Any optical device for human vision correction that corrects for astigmatism, a very common human vision defect, requires aspheric surfaces if the optical device is based on prior art using conventional refractive surfaces. However, correction of such defects with the present invention requires only a modification in the optical axis orientation pattern, as exemplified in FIG. 2B, which shows the pattern required for a correction of a particular instance of focus and astigmatism. The example of FIG. 2B shows the optical axis pattern near the optical axis of a diffractive waveplate lens designed to correct for 3 diopters of focus error and −2 diopters of astigmatism.

Figure 3:
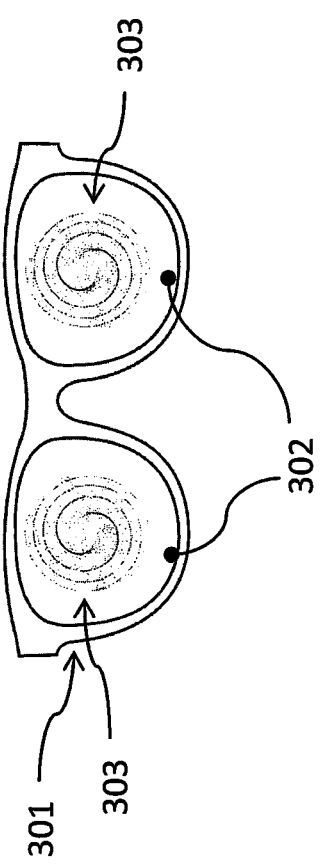
FIG. 3 illustrates an example of spectacles with locally flat substrates, wherein human vision is corrected based on thin films of an optically active material with a pattern of optical axis orientation.

Referring to FIG. 3, spectacles 301 with two lenses 302, one for the right eye and one for the left eye, according to the present invention can be constructed based on optical axis orientation patterns 303. Although the particular patterns 303 of optical axis orientation shown in FIG. 3 represent lenses that correct only for focus, only a change in the pattern is required in order to correct for other human vision defects, including, for example, astigmatism.

Figure 4B:
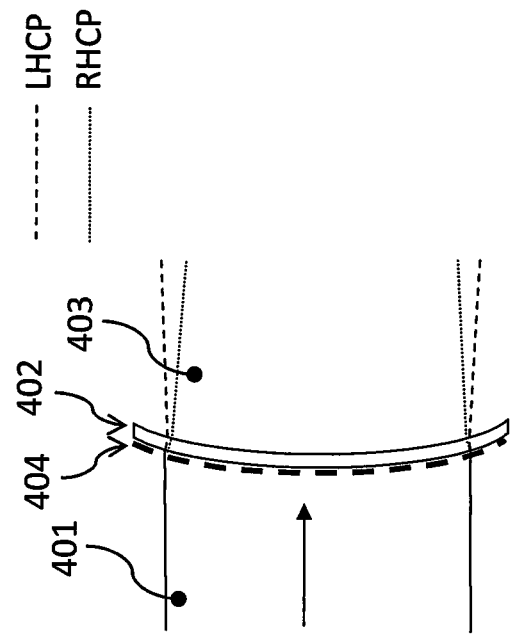
FIG. 4B illustrates a side view of an optical substrate that is locally flat, for use in vision correction devices such as spectacles, sunglasses, skiing goggles, swimming goggles, or goggles for protection of the eyes from ballistic projectiles.
Figure 4A:
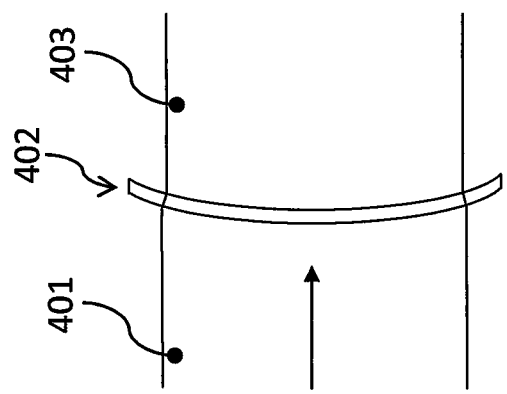
FIG. 4A illustrates a side view of an optical substrate that is locally flat, for use in vision correction devices such as spectacles, sunglasses, skiing goggles, swimming goggles, or goggles for protection of the eyes from ballistic projectiles.
Figure 4C:
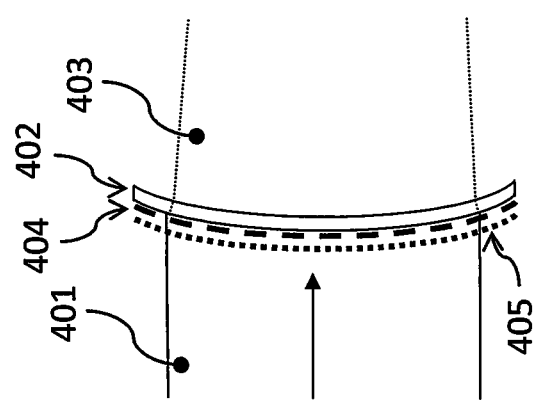
FIG. 4C illustrates a side view of an optical substrate that is locally flat, for use in vision correction devices such as spectacles, sunglasses, skiing goggles, swimming goggles, or goggles for protection of the eyes from ballistic projectiles.

Referring to FIG. 4, the operation of one of the lenses of an ophthalmic lens device for human vision correction is illustrated. In FIG. 4A, the light 401 from a distant point in a scene is shown incident on the lens 402. In FIG. 4A, there is no coating on or in the lens to deflect the path of the incident light, so the light 403 after passage through the lens is propagating in the same direction as it was prior to being incident on the lens. In FIG. 4B, a diffractive waveplate coating 404 has been added, resulting in a focusing effect (i.e. positive focal length) on right-hand circularly polarized (RHCP) light, and a defocusing effect (i.e. negative focal length) on left-hand circularly polarized (LHCP) light. In FIG. 4C, a multilayer structure 405 has been added, consisting of a linear polarizer followed by a broadband quarter-wave plate, having the effect of producing RHCP light, thereby eliminating the LHCP light and assuring that all of the light reaching the user's eye has the same focal properties. If the optical axis pattern in coating 404 in FIG. 4B is matched to the user's eye, all the aberrations that are correctable using prior art are also correctable using such diffractive waveplate coatings. The aberrations that can be corrected using diffractive waveplate coatings include, for example, astigmatism and focus error.

Figure 5C:
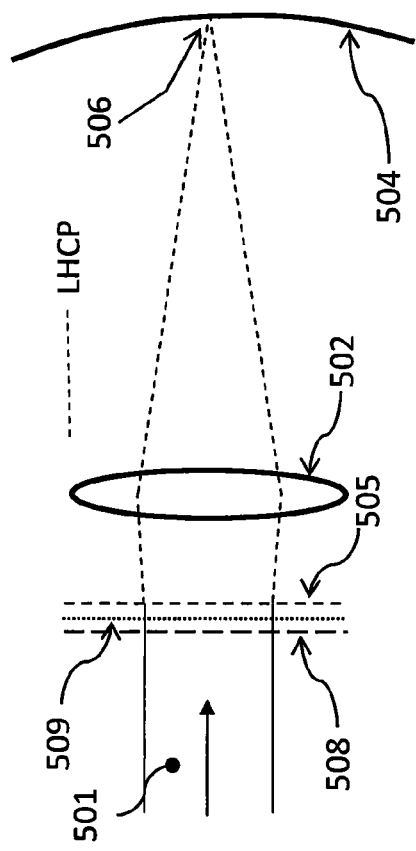
FIG. 5C illustrates an example of correction of myopia (nearsightedness) in a human eye using a thin film of anisotropic material with a pattern of optical axis orientation designed to focus or defocus light incident on the eye.

Referring to FIG. 5, the correction of myopia (nearsightedness) with a diffractive waveplate coating is illustrated. In FIG. 5A, light 501 is incident from a distant object onto the human eye lens 502, and because of the person's myopia, the light is brought to a focus 503 in front of the person's retina 504. In FIG. 5B, a diffractive waveplate coating 505 is introduced into the path of the light, resulting in shortening of the focal distance for RHCP light, and lengthening of the focal distance for LHCP light. This brings the LHCP light into focus on the person's retina at location 506, and results the RHCP light being even more out-of-focus than it was without the diffractive coating in the beam path, coming to a focus at location 507. In FIG. 5C, two additional thin-film coatings have been introduced into the light path, a linear polarizer 508 and a broadband quarter-wave plate 509, resulting in only LHCP light being incident on the diffractive waveplate coating 505, on the person's eye lens 502, and on the person's retina 504. Therefore in the configuration of FIG. 5C, all of the light that reaches the user's eye is brought to a focus at location 506 on the user's retina, resulting in a single sharp image of the scene.

The thin films 508 (linear polarizer), 509 (homogeneous broadband quarter-wave plate), and 505 (diffractive patterned waveplate) in FIG. 5C are shown without any supporting substrate, although in practice such a substrate must be provided to support these thin-film elements, and to provide an interface to the frame by which the vision correction device is fixed relative to the user's eye. There are many possible configurations, as will be evident to those skilled in the art that could provide such support to the referenced thin-film coatings.

Figure 6A:
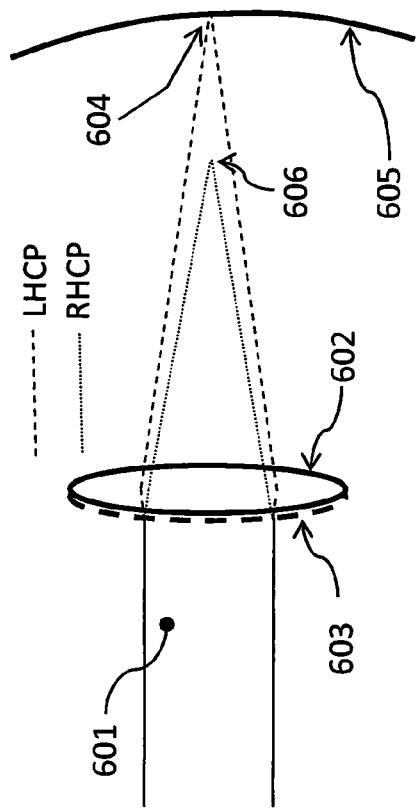
FIG. 6A illustrates an example of an intraocular lens that includes a thin-film diffractive waveplate lens coating that produces a dual-focus image on the user's retina, one image for near objects and one image for far objects.

Referring to FIG. 6, the use of a thin-film diffractive waveplate coating on an intraocular lens is illustrated. In FIG. 6A, unpolarized light 601 from a distant object is incident on the surgically-implanted conventional intraocular lens 602, which is coated with a thin-film patterned diffractive waveplate coating 603 that causes slight focusing of right-hand circularly polarized (RHCP) light, and slight defocusing of left-hand circularly polarized (LHCP) light. Due to this differential focusing effect, LHCP light from the distant object is brought to a focus 604 on the use's retina 605, while RHCP light is brought to a focus 606 in front of the user's retina 605.

Figure 6B:
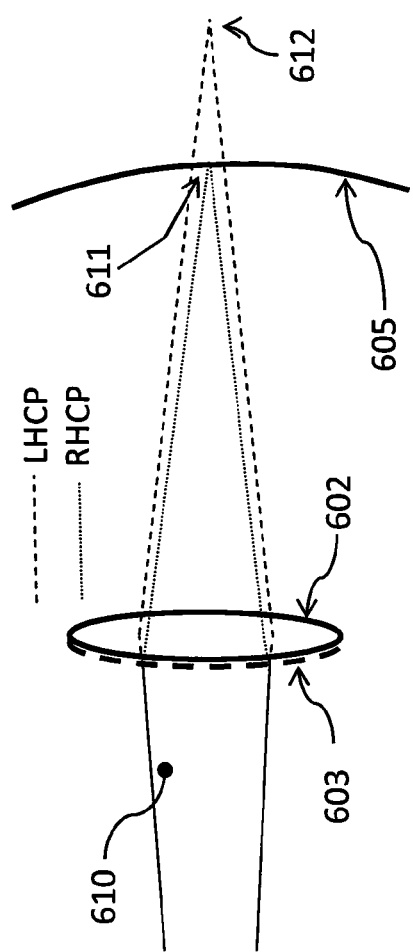
FIG. 6B illustrates an example of an intraocular lens that includes a thin-film diffractive waveplate lens coating that produces a dual-focus image on the user's retina, one image for near objects and one image for far objects.

As illustrated in FIG. 6B, unpolarized light 610 from a nearby object is differentially focused by the combination of the conventional refractive intraocular lens 602 and the diffractive waveplate lens 603, resulting in RHCP light from the nearby object being brought to a focus 611 on the user's retina 605, and LHCP light from the nearby object being brought to a focus 612 behind the user's retina 605.

FIGS. 6A and 6B together illustrate the dual-focus nature of the combination of the conventional refractive intraocular lens 602 and the patterned diffractive waveplate coating 603, providing focused images for both near and far objects. While dual-focus or multi-focus intraocular lens structures have been available from prior art, the present invention discloses two advantages of the use of diffractive waveplate coatings to provide such multi-focal functionality. One is the simplicity, and therefore cost advantages, of using a diffractive waveplate coating to provide this functionality, compared with all prior art methods.

Figure 6C:
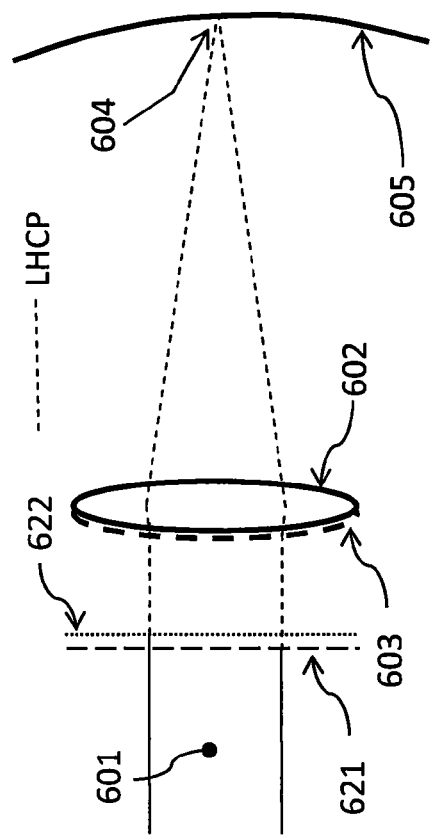
FIG. 6C illustrates an example of an intraocular lens that includes a thin-film diffractive waveplate lens coating that produces a dual-focus image on the user's retina, one image for near objects and one image for far objects.

The other advantage is illustrated in FIG. 6C, showing the elimination of one of the images by means of an additional external optic such as circularly-polarizing sunglasses with no optical power, illustrated in FIG. 6C as a linear polarizer 621 and a homogeneous broadband quarter-wave plate 622. With prior art techniques, it is impractical to eliminate either of the two images produced by a dual-focus intraocular lens by means of externally-worn optics such as a polarizer, but with the invention herein disclosed, the undesired image can be eliminated by means of externally-worn polarizing optics. As anyone skilled in the art will appreciate, elimination of the undesired defocused image produced by a multi-focal intraocular lens will improve the quality of the image perceived by the user. Thus, the disclosed invention has a highly desirable degree of flexibility not available with prior art techniques for the design and fabrication of multifocal intraocular lenses.

Figure 7A:
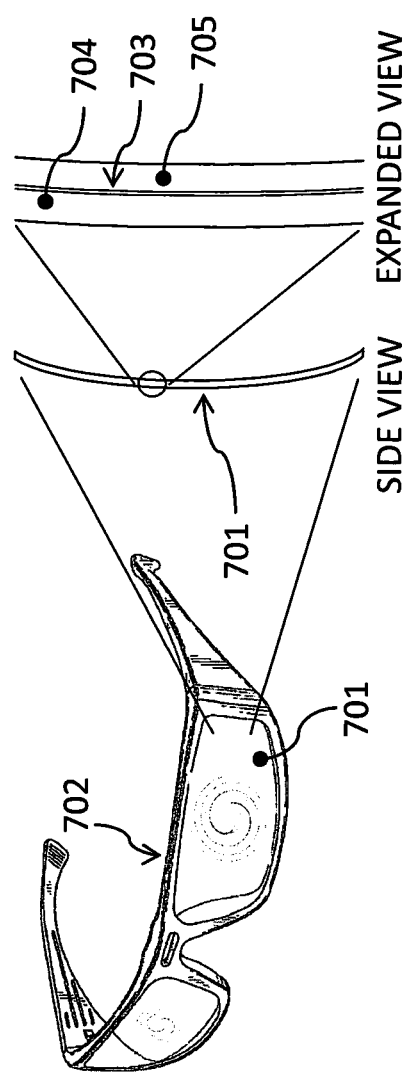
FIG. 7A illustrate an example of sunglasses with locally flat substrates, in which human vision is corrected by a thin film of anisotropic material laminated between the two parts of the substrate constituting the lenses of the sunglasses.

FIG. 7 illustrates one embodiment of the layered structure of an optical device for human vision correction. As illustrated in FIG. 7A, the transparent portion 701 of the optical device is contained within a frame 702. The optically-active layer 703 is contained between locally flat outer substrate 704 and inner substrate 705. In this context, "outer" means the side of the lens furthest from the eye, and "inner" means the side of the lens closest to the eye.

Figure 7B:
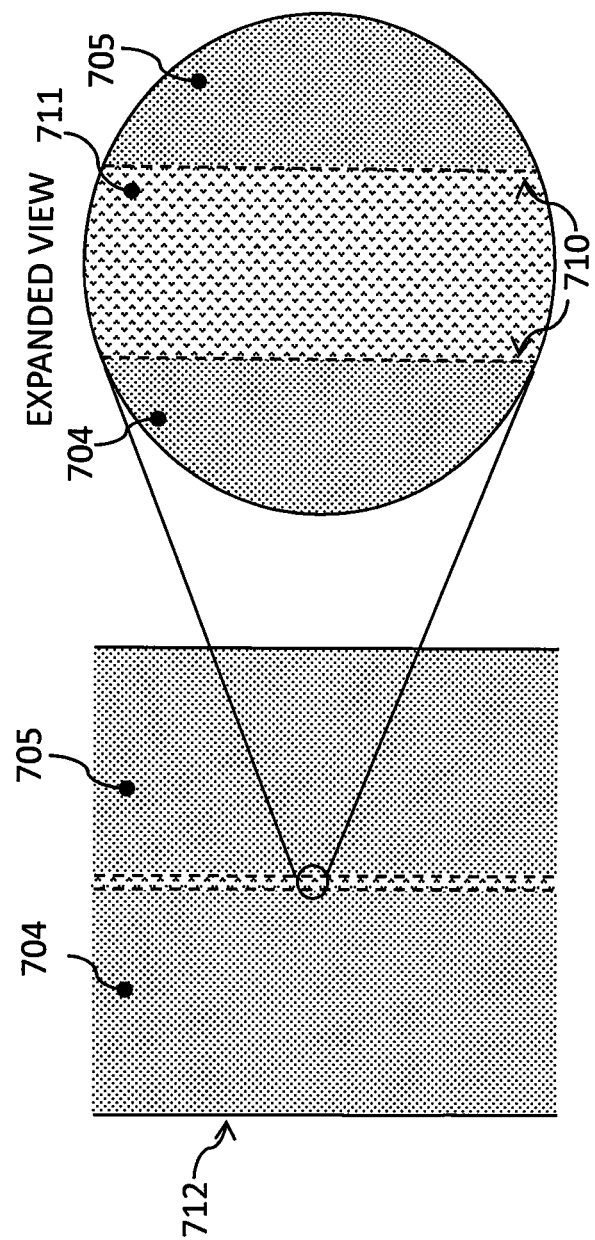
FIG. 7B illustrate an example of sunglasses with locally flat substrates, in which human vision is corrected by a thin film of anisotropic material laminated between the two parts of the substrate constituting the lenses of the sunglasses.

In the preferred embodiment illustrated in FIG. 7B, a universal blank set of sunglasses is stored at the point of sale in the form of the layered structure including photoalignment layers 710 and polymerizable liquid crystal 711. Once the required measurements have been made on the customer's eyes, the photoalignment layers 710 are written by means of a specially constructed programmable optical system that aligns the photoalignment layers 710 with a pattern of linearly polarized light designed to correct the aberrations of the customer's eye. After this optical axis pattern is written, the polymerizable liquid crystal 711 aligns itself to the photoalignment layers 710, after which UV radiation is used to polymerize the polymerizable liquid crystal 711. The outer layer 712 of the outer substrate 704 may include a linear polarizer and broadband quarter-wave plate as noted in the discussions of FIG. 4C, FIG. 5C, and FIG. 6C, thus assuring that the optical correction is the same for all the light reaching the user's eye. Additional functionality, such as additional light filtering if the optical device is a part of sunglasses, anti-reflection coatings, and a hard coating to prevent scratches, could be incorporated into or on the outer substrate 704 and/or the inner substrate 705.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An ophthalmic lens device comprising: a diffractive waveplate polymerized liquid crystal coating that simultaneously focuses right-hand circularly polarized light and defocuses left hand circularly polarized light, or that simultaneously focuses left-hand circularly polarized light and defocuses right-hand circularly polarized light;
a substrate on which the diffractive waveplate coating is deposited or contained within as a diffractive waveplate lens with a spatially changing optical axis orientation pattern; and
a mechanical feature to securely position the ophthalmic lens device to be adapted to correct vision of a user's eye with the device, the ophthalmic lens device adapted to be not located on a surface of the user's eye.

2. The ophthalmic lens device of claim 1 further comprising:
a layer for selecting light of one polarization.

3. The ophthalmic lens device of claim 2 further comprising:
one or more layers for attenuating a brightness of a scene.

4. The ophthalmic lens device of claim 1 wherein a focal power of the diffractive waveplate lens varies progressively based on a viewing angle of a user.

5. The ophthalmic lens device of claim 1 wherein the differential focusing properties of the diffractive waveplate coating for light of different polarizations results in focused images for both near and far objects.

6. The ophthalmic lens device of claim 1 wherein the ophthalmic lens device is incorporated into an eyewear for use while swimming or underwater.

7. The ophthalmic lens device of claim 1 wherein the ophthalmic lens device is incorporated into an eyewear for use while skiing.

8. The ophthalmic lens device of claim 1 wherein the ophthalmic lens device is incorporated into an eyewear for protection of the eye from a ballistic projectile.

9. An ophthalmic lens device comprising: one or more refractive surfaces that partially correct a user's vision defect;
a diffractive waveplate polymerized liquid crystal coating that simultaneously focuses right-hand circularly polarized light and defocuses left-hand circularly polarized light, or that simultaneously focuses left-hand circularly polarized light and defocuses right-hand circularly polarized light, which are not corrected by the one or more refractive surfaces;
a substrate on which the diffractive waveplate coating is deposited, or within which the diffractive coating is contained with a spatially changing optical axis orientation pattern; and
a mechanical feature to securely position the ophthalmic lens device to be adapted to correct a user's vision, and is adapted to be not located on a surface of an eye.

10. The ophthalmic lens device of claim 9 further comprising:
a layer for selecting light of a polarization.

11. The ophthalmic lens device of claim 10 further comprising:
one or more layers for attenuating a brightness of a scene.

12. The ophthalmic lens device of claim 9 wherein the diffractive waveplate lens is incorporated into an eyewear for use while swimming or underwater.

13. The ophthalmic lens device of claim 9 wherein the diffractive waveplate lens is incorporated into an eyewear for use while skiing.

14. The ophthalmic lens device of claim 9 wherein the ophthalmic lens device is incorporated into an eyewear for protection of the eye from a ballistic projectile.

15. The ophthalmic lens device of claim 1, wherein the diffractive waveplate coating includes a differential focusing effect, wherein the left hand circularly polarized light from a distant object is adapted to be brought into focus on a retina of the user's eye, while the right hand circularly polarized light is adapted to be brought into focus in front the retina of the user's eye.

16. The ophthalmic lens device of claim 9, wherein the diffractive waveplate coating includes a differential focusing effect, wherein the left hand circularly polarized light from a distant object is adapted to be brought into focus on a retina of the user's eye, while the right hand circularly polarized light is adapted to be brought into focus in front the retina of the user's eye.

17. An ophthalmic lens device comprising:
a diffractive waveplate polymerized liquid crystal coating that focuses right-hand circularly polarized light and defocuses left hand circularly polarized light, or that simultaneously focuses left-hand circularly polarized light and defocuses right-hand circularly polarized light;

a substrate on which the diffractive waveplate coating is deposited or contained within as a diffractive waveplate lens with a spatially changing optical axis orientation pattern; and a mechanical implant adapted to securely position the ophthalmic lens device within a user's eye to be adapted to correct vision of a user's eye with the device, the ophthalmic lens device adapted to be not located on a surface of the user's eye.

18. The ophthalmic lens device of claim 17, wherein the diffractive waveplate coating includes a differential focusing effect, wherein both left hand circularly polarized light from a distant object and right hand circularly polarized light from a near object are adapted to be brought into focus on a retina of the user's eye, thereby providing a dual-focus image on the user's retina with one image for near objects and one image for far objects.

* * * * *